United States Patent [19]

Larsen

[11] 4,442,260

[45] Apr. 10, 1984

[54] PREPARATION OF SALT SOLUTION USEFUL FOR MAKING NYLON

[75] Inventor: Howland A. Larsen, Parkersburg, W. Va.

[73] Assignee: E. I. Du Pont de Nemours & Company, Wilmington, Del.

[21] Appl. No.: 475,030

[22] Filed: Mar. 14, 1983

[51] Int. Cl.³ .............................................. C08G 69/28
[52] U.S. Cl. .................................... 524/845; 252/182; 260/501.2; 528/335
[58] Field of Search ........................ 528/335; 524/845; 252/182; 260/501.2

[56] References Cited

U.S. PATENT DOCUMENTS

| | | | |
|---|---|---|---|
| 3,027,355 | 3/1962 | Taul et al. | 528/335 |
| 3,253,892 | 5/1966 | Brignac et al. | 528/335 |
| 3,269,990 | 8/1966 | Wiloth et al. | 526/71 |
| 3,296,217 | 1/1967 | Tate | 526/71 |
| 3,502,624 | 3/1970 | Flack et al. | 524/845 |
| 4,131,712 | 12/1978 | Sprauer | 528/335 |
| 4,213,884 | 7/1980 | Eckell et al. | 260/29.2 |
| 4,233,234 | 11/1980 | Rotzoll et al. | 528/335 |
| 4,251,653 | 2/1981 | Eckell et al. | 528/335 |

Primary Examiner—C. Warren Ivy

[57] ABSTRACT

A process is described for making highly concentrated solutions of nylon salt in which the diamine is added in two portions, one before and one after a step in which water is evaporated from a solution of maximum solubility.

1 Claim, 1 Drawing Figure

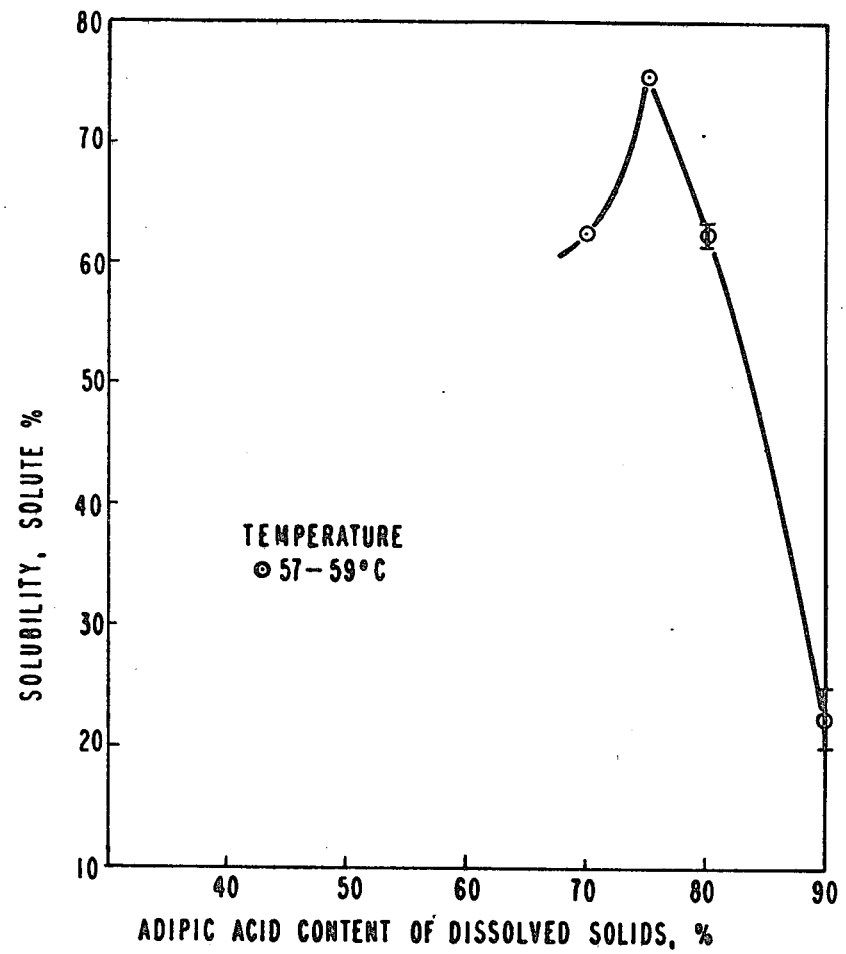

PREPARATION OF SALT SOLUTION USEFUL FOR MAKING NYLON

BACKGROUND OF THE INVENTION

In the preparation of long-chain polyamides, ordinarily a salt solution of a dicarboxylic acid and a diamine is heated until the diamine-dicarboxylic acid salt begins polymerizing by polycondensation to form long chain polyamides.

Normally, the salt solution is prepared containing stoichiometric amounts of diamine and diacid (which is about 56% diacid and 44% diamine by weight). Normally also, the salt solution is prepared to contain about 50% or so by weight solute content, and is then stored temporarily or is transferred to a prepolymerization vessel to await polymerization. It is concentrated to 70–80% solute by evaporating water before polymerization begins. The reason the solution is not made up at 70–80% solute concentration orginally is because at 70–80% solute concentration, the solution must be maintained at about 130°–160° C. to keep the solute in solution. At these temperatures discoloration and some polymerization occurs.

Thus, it has been a goal of researchers in the field to increase the solute concentration of these solutions prior to polymerization without having to maintain them at high temperatures. If the solute concentration can be increased less water will be present, thus reducing energy needs for water removal during the concentrating step. Moreover, heretofore, the solutions could not be concentrated beyond about 70–80% solute by weight because at the temperatures required to concentrate the salt solution further, polymerization began.

Thus the polymerization reaction heretofore was being conducted on salt solutions containing about 20–30% water by weight. This was not advantageous for several reasons. First the polycondensation reaction between diacids and diamines to form polyamides also forms water, and inasmuch as the reaction is an equilibrium reaction any water present must be removed before polymerization can proceed. Doing so increases the space-time of the polymerization step and leads to much greater energy requirements.

SUMMARY OF THE INVENTION

If the initial salt solution contains a certain selected excess of adipic acid (which depends on the temperature of the solution), more solute can be dissolved in the initially prepared salt solution than heretofore had been believed possible. For example, at a solution temperature of 55°–60° C. and a salt composition of 73.5 to 77.5% by weight adipic acid and 22.5–26.5% by weight hexamethylene diamine, a solution containing about 60–69% by weight solute can be prepared. Ordinarily if stoichiometric amounts of diacid and diamine (i.e., 56% diacid and 44% diamine) are dissolved, the maximum solute concentration obtainable at 55°–60° C. is only about 59% by weight (over 59%, the solute begins to precipitate).

Preparation of salt having the composition which exhibits maximum solubility as described above leads to two important advantages. First, the amount of water required in the initial salt solution which must later be removed by evaporation is reduced. Second, during evaporation of the water prior to polymerization much higher solute concentrations can be achieved. Thus the solution of about 60–69% solute referred to above can be concentrated (preferably by evaporation of water at a temperature between 125°–155° C. and a pressure between 0.8 and 1.2 atmospheres) to obtain a concentrated solution in which the solute comprises between about 89 and 96%, preferably 93–96%, by weight of the solution. In contrast to usual solutions that contain stoichiometric amounts of adipic acid and hexamethylene diamine (in which the solute begins to precipitate when the concentration of solute reaches 70–80% by weight), the concentrated solution obtained herein retains the solute in solution even though the solute concentration can be between 93 and 96%.

When the concentrated solution is ready to be polymerized, hexamethylene diamine (HMD) is simply added until both HMD and adipic acid are present in about equimolar (i.e. stoichiometric) proportions.

DESCRIPTION OF THE DRAWING

The drawing depicts the solubility curve of mixtures of HMD and adipic acid in water at a temperature of 57°–59° C.

DETAILED DESCRIPTION OF THE INVENTION

Concentrated salt solutions suitable for making 66 nylon (i.e., the polymer made from hexamethylene diamine and adipic acid), can be made by the process of this invention.

The first step of the process is to prepare an aqueous solution in which the solute phase contains 73.5–77.5% adipic acid and 22.5–26.5% hexamethylene diamine, by weight. This solution is prepared at 55°–60° C. to contain from 60–69% of such a solute, by weight, plus 31–40% water. Because of the unexpectedly sharp maximum in the solubility-composition curve for this system, as shown in the drawing and explained below, the specified composition range is uniquely and surprisingly well suited for preparing solutions with minimum (i.e., 31–40%) water content at conveniently attainable temperatures of 55°–60° C. where the rate of undesired side reactions to form colored by-products is minimized.

The second step of the process is to remove water from the solution prepared in the first step by evaporation until the solution contains from between 89 to 96%, preferably 93–96%, by weight solute. Unlike evaporation of salt solutions in which the adipic acid and hexamethylene diamine are present in equimolar proportion, there is essentially no loss of hexamethylene diamine in this step. Furthermore, the unique solubility of the salt solution prepared in the first step permits the use of evaporation temperatures much lower than those required to maintain solubility when the salt is an equimolar composition of the HMD and the adipic acid and evaporation to comparable solute concentration is conducted. Advantages of this lower temperature are the prevention of prepolymer formation which will foul evaporator surfaces and the fact that lower evaporator temperatures are more economical.

When the concentrated solution is ready to be polymerized, hexamethylene diamine, which may contain 0–20% water, is added to the concentrated salt made in the second step. This addition is controlled so that the final composition will contain hexamethylene diamine and adipic acid in very nearly equimolar proportions, preferably at a total salt concentration of 87–97% by weight. The addition can take place in a conventional batch polymerization vessel such as an autoclave. It can also take place continuously in a small, agitated vessel where average residence time is kept below 10 minutes so that prepolymer formation is minimized to the point that vessel fouling does not take place. In this instance a modest amount of heat must be added either to the vessel or to one or both of the feed streams to achieve in the vessel a temperature above 190° C., the minimum required to keep the salt in solution.

As seen from the drawing, when the adipic acid content of solute present is between about 73.5–77.5% by weight, then the amount of adipic acid-hexamethylene diamine salt that can be dissolved suddenly increases and reaches a sharp peak. It is the unexpected increase in solubility that enables one to obtain the high salt concentrations described herein. Once the initial salt solution is prepared it is ordinarily stored until it is ready to be polymerized. Just prior to polymerization most of the water is removed by evaporation thus reducing the energy requirement and reducing the required space-time of the subsequent polymerization. The solution is preferably concentrated by evaporating water at atmospheric pressures, although higher or lower pressures can be used, as e.g. 0.5 atm to 1.7 atm ($5.1 \times 10^4 - 17.0 \times 10^4$ PA). The evaporation is ordinarily carried out by boiling the solution at 110°–160° C. (preferably at 125°–155° C.). The evaporation is continued until the solute content reaches 89 to 96% by weight.

Once the solution has been concentrated, hexamethylene diamine is added until the amounts of hexamethylene diamine and adipic acid present reach stoichiometric proportions. The hexamethylene diamine can be added molten or in a water solution of 80% or more hexamethylene diamine. By stoichimetric proportions is meant that the mole ratio of hexamethylene diamine to adipic acid is between about 0.97/1 to 1.03/1 and preferably 0.99/1 to 1.01/1.

The final salt solution is useful to make 66 nylon on heating to induce polymerization of the salt.

The increase in solubility of the solute in the presence of a selected excess of adipic acid is seen in the drawing which is a graph that plots % solubility of solute versus % adipic acid content of dissolved salt. It is seen that as adipic acid content increases from about 67.5% to about 75% when tne temperature of the solution is between 57°–59° C., the solubility of the solids suddenly increases and reaches a peak of about 75 or 76%. From there the solubility decreases sharply as adipic acid content increases. Thus at about 57°–59° C. solution temperature a peak in solubility occurs when the adipic acid content of the solute is between about 73.5 and 77.5% by weight (the hexamethylene diamine content being between 22.5 and 26.5% by weight).

EXAMPLE

First Step

A salt solution was prepared by adding 60.02 pounds ($2.72 \times 10^4$ gm) adipic acid, and 19.89 pounds ($9.02 \times 10^3$ gm) hexamethylene diamine to 45.09 pounds ($2.05 \times 10^4$ gm) water at a temperature of 50°–65° C. This produces a solution containing 63.9% by weight solute which consisted of 75.1% by weight adipic acid and 24.9% by weight hexamethylene diamine. The solution was maintained at 50°–65° C. until the second step was carried out.

Second Step

The solution obtained in the first step was pumped into a stirred autoclave having a volume of about 43 gal (163 liters). The agitator was turned on and heat was applied with the vent valve open. Heating was continued as steam evolved, until the temperature of the liquid in the autoclave reached 125° C. At this point the solute concentration of the solution in the autoclave was about 89% by weight, as determined by subsequent observations which established temperature and % solute relationships.

Subsequent Steps

The solute was polymerized without removing it from the autoclave. The vent was closed and 35.00 lb. ($1.59 \times 10^4$ gm) of 80.34% hexamethylene diamine in water was forced into the autoclave in several portions using an additive pot and steam as the driving force. The autoclave was heated to 201° C. at which point pressure had risen to 180 psig ($1.34 \times 10^6$ PA). Pressure was decreased to atmospheric pressure at a rate of 3.1 psi/min ($3.56 \times 10^2$ PA/s). Temperature had risen to 242° C. by the time pressure had reached one atmosphere. With pressure at one atmosphere heating was continued using Dowtherm ® at 327° C. in the jacket of the autoclave for another 45 min. At the end of this period, temperature in the autoclave had risen to 270° C. Polymer produced was then forced from the autoclave using nitrogen. The resulting polymer had high molecular weight as indicated by a relative viscosity of 39.5 as measured at 8.4% polymer in 90% formic acid solution. Further analysis indicated that the polymer made contained 43.5 acid equivalents and 79.1 amine equivalents per million grams of polymer.

I claim:
1. A process for making 66-nylon salt solution which comprises, in sequence
   (a) preparing a water solution in which the solute phase contains 73.5–77.5% adipic acid and 22.5–26.5% hexamethylene diamine, by weight, at a temperature of 55°–60° C. in which the total solute concentration is 60–69% and the water concentration is 31–40%, and
   (b) concentrating the solution by evaporating water until the solute comprises between 89 and 96%, by weight, and
   (c) adding hexamethylene diamine until the hexamethylene diamine and adipic acid are in about stoichiometric proportions.

* * * * *